(12) United States Patent
Roessler et al.

(10) Patent No.: US 6,869,494 B2
(45) Date of Patent: Mar. 22, 2005

(54) METHOD FOR MAKING A DISPOSABLE GARMENT HAVING SOFTER WAIST AND LEG CUFFS

(75) Inventors: Thomas Harold Roessler, Menasha, WI (US); Michael Tod Morman, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 322 days.

(21) Appl. No.: 10/025,071

(22) Filed: Dec. 19, 2001

(65) Prior Publication Data

US 2003/0114817 A1 Jun. 19, 2003

(51) Int. Cl.$^7$ .......................... B32B 31/00; A61F 13/15
(52) U.S. Cl. ....................... 156/201; 156/164; 156/265; 156/229; 156/202; 156/213; 156/204; 156/227; 156/494; 156/301; 156/302; 156/461; 156/519; 604/385.01
(58) Field of Search ................................. 156/164, 461, 156/519, 494, 169, 229, 301, 302, 265, 270, 201, 202, 204, 213, 227; 604/385.01

(56) References Cited

U.S. PATENT DOCUMENTS

| | | | |
|---|---|---|---|
| 4,055,182 A | 10/1977 | Mack | 128/287 |
| 4,239,578 A | 12/1980 | Gore | |
| 4,364,787 A | 12/1982 | Radzins | |
| 4,379,016 A | 4/1983 | Stemmler et al. | |
| 4,381,781 A | 5/1983 | Sciaraffa et al. | |
| 4,397,704 A | 8/1983 | Frick | |
| 4,407,284 A | 10/1983 | Pieniak | |
| 4,464,217 A | 8/1984 | Dickover et al. | |
| 4,515,595 A | 5/1985 | Kievit et al. | |
| 4,543,154 A | 9/1985 | Reiter | |
| 4,606,964 A | 8/1986 | Wideman | |
| 4,618,384 A | 10/1986 | Sabee | |
| 4,663,220 A | 5/1987 | Wisneski et al. | |
| 4,704,116 A | 11/1987 | Enloe | |
| 4,710,189 A | 12/1987 | Lash | |
| 4,798,603 A | 1/1989 | Meyer et al. | |

(List continued on next page.)

FOREIGN PATENT DOCUMENTS

| | | |
|---|---|---|
| EP | 217 032 | 4/1987 |
| EP | 417 766 | 3/1991 |
| EP | 437 771 | 7/1991 |
| EP | 650 714 | 5/1995 |
| EP | 682 930 | 11/1995 |
| EP | 750 893 | 1/1997 |
| EP | 820 747 | 1/1998 |
| EP | 1 179 330 | 2/2002 |
| EP | 1 188 427 | 3/2002 |
| EP | 1 228 741 | 8/2002 |
| WO | 95/16425 | 6/1995 |
| WO | WO 95/19258 A1 | 7/1995 |
| WO | WO 96/10481 | 4/1996 |
| WO | WO 00/38911 | 7/2000 |
| WO | WO 01/15646 A1 | 3/2001 |
| WO | 01/91685 | 12/2001 |
| WO | 01/92013 | 12/2001 |

*Primary Examiner*—Linda L Gray
(74) *Attorney, Agent, or Firm*—David J. Arteman; Alyssa A. Dudkowski

(57) ABSTRACT

The present invention provides a method of achieving low tension, highly conformable elasticized areas in a nonwoven web construction such as may be suitable for the waistbands or leg openings of disposable absorbent pant garments, cuffs on sleeves of medical garments, or the like. A web, or webs, of nonwoven material which make up the substrate for the elasticized area are provided to be very light weight and flexible and provide the minimal amount of substrate to which an elastomeric liquid barrier material is affixed. The absorbent, or liquid retention, section of an absorbent garment article made according to the present invention will have its own barrier layer facing the backsheet, in order that the backsheet may be composed of a light and conformable material.

25 Claims, 4 Drawing Sheets

U.S. PATENT DOCUMENTS

| | | |
|---|---|---|
| 4,808,176 A | 2/1989 | Kielpikowski |
| 4,813,946 A | 3/1989 | Sabee |
| 4,816,026 A | 3/1989 | Richardson |
| 4,834,741 A | 5/1989 | Sabee |
| 4,895,568 A | 1/1990 | Enloe |
| 4,908,247 A | 3/1990 | Baird et al. |
| 4,917,682 A | 4/1990 | Lancaster et al. |
| 4,925,520 A | 5/1990 | Beaudoin et al. |
| 4,938,753 A | 7/1990 | Van Gompel et al. |
| 4,938,821 A | 7/1990 | Soderlund et al. |
| 4,965,122 A | 10/1990 | Morman |
| 4,968,313 A | 11/1990 | Sabee |
| 5,167,897 A | 12/1992 | Weber et al. |
| 5,176,668 A | 1/1993 | Bernardin |
| 5,176,672 A | 1/1993 | Bruemmer et al. |
| 5,192,606 A | 3/1993 | Proxmire et al. |
| 5,226,992 A | 7/1993 | Morman |
| 5,254,111 A | 10/1993 | Cancio et al. |
| 5,340,424 A | 8/1994 | Matsushita |
| 5,364,382 A | 11/1994 | Latimer et al. |
| 5,399,219 A | 3/1995 | Roessler et al. |
| 5,405,342 A * | 4/1995 | Roessler et al. ............ 604/364 |
| 5,407,507 A | 4/1995 | Ball |
| 5,415,644 A | 5/1995 | Enloe |
| 5,429,629 A | 7/1995 | Latimer et al. |
| 5,486,166 A | 1/1996 | Bishop et al. |
| 5,490,846 A | 2/1996 | Ellis et al. |
| 5,496,298 A | 3/1996 | Kuepper et al. |
| 5,509,915 A | 4/1996 | Hanson et al. |
| 5,531,729 A | 7/1996 | Coles et al. |
| 5,540,796 A | 7/1996 | Fries |
| 5,595,618 A | 1/1997 | Fries et al. |
| 5,649,919 A | 7/1997 | Roessler et al. |
| 5,683,531 A * | 11/1997 | Roessler et al. ............ 156/164 |
| 5,700,255 A | 12/1997 | Curro et al. |
| 5,743,994 A | 4/1998 | Roessler et al. |
| 5,827,259 A | 10/1998 | Laux et al. |
| 5,846,232 A | 12/1998 | Serbiak et al. |
| 5,910,224 A | 6/1999 | Morman |
| 6,050,985 A | 4/2000 | Lavon et al. |
| 6,077,254 A | 6/2000 | Silwanowicz et al. |
| 6,156,421 A | 12/2000 | Stopper et al. |
| 6,183,847 B1 | 2/2001 | Goldwasser |
| 6,231,557 B1 | 5/2001 | Krautkramer et al. |
| 6,245,050 B1 | 6/2001 | Odorzynski et al. |
| 6,264,641 B1 | 7/2001 | Van Gompel et al. |
| 2003/0114825 A1 | 6/2003 | Morman et al. |
| 2003/0114826 A1 | 6/2003 | Roessler et al. |

* cited by examiner

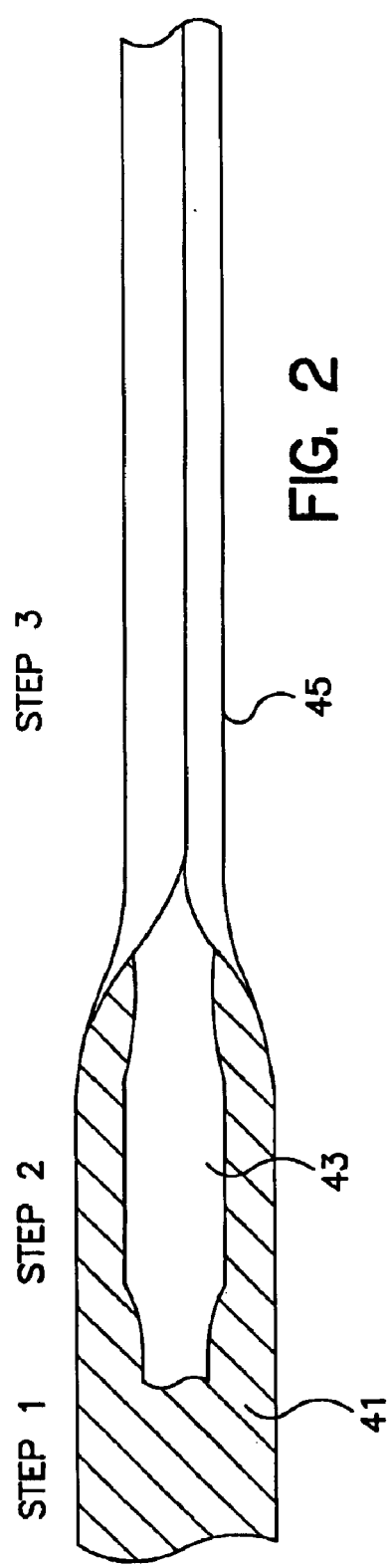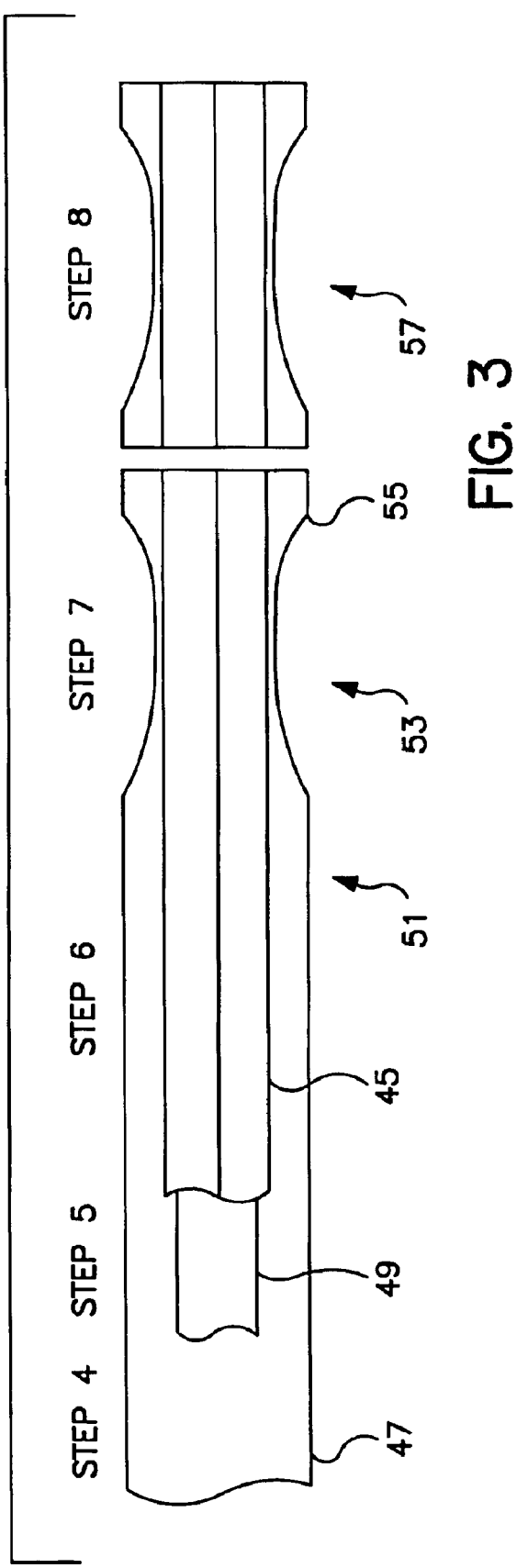

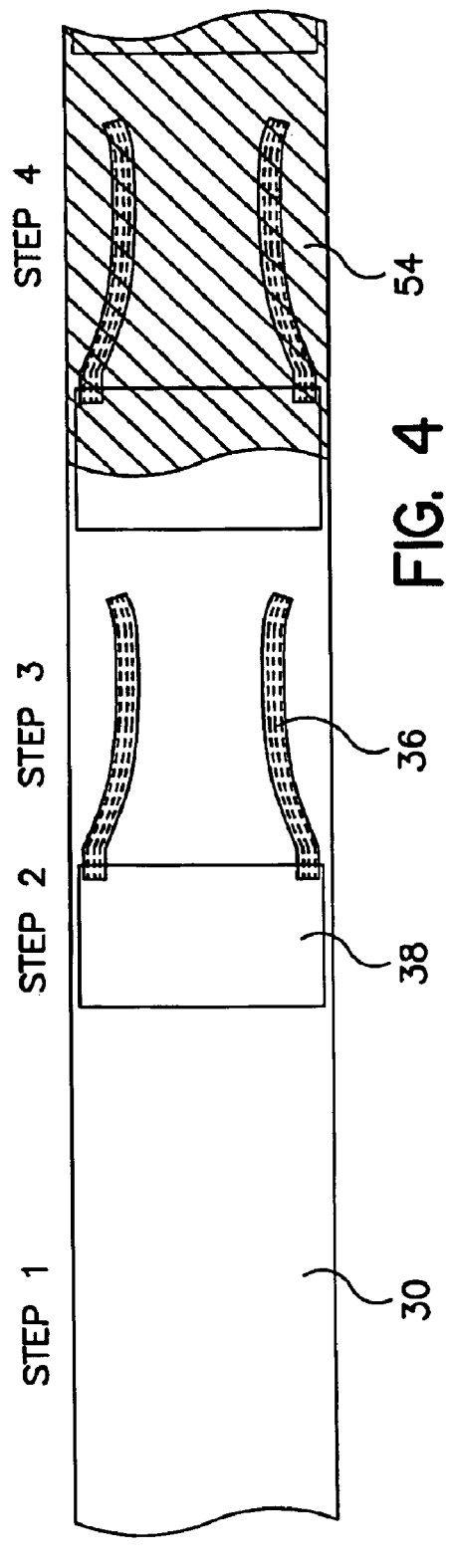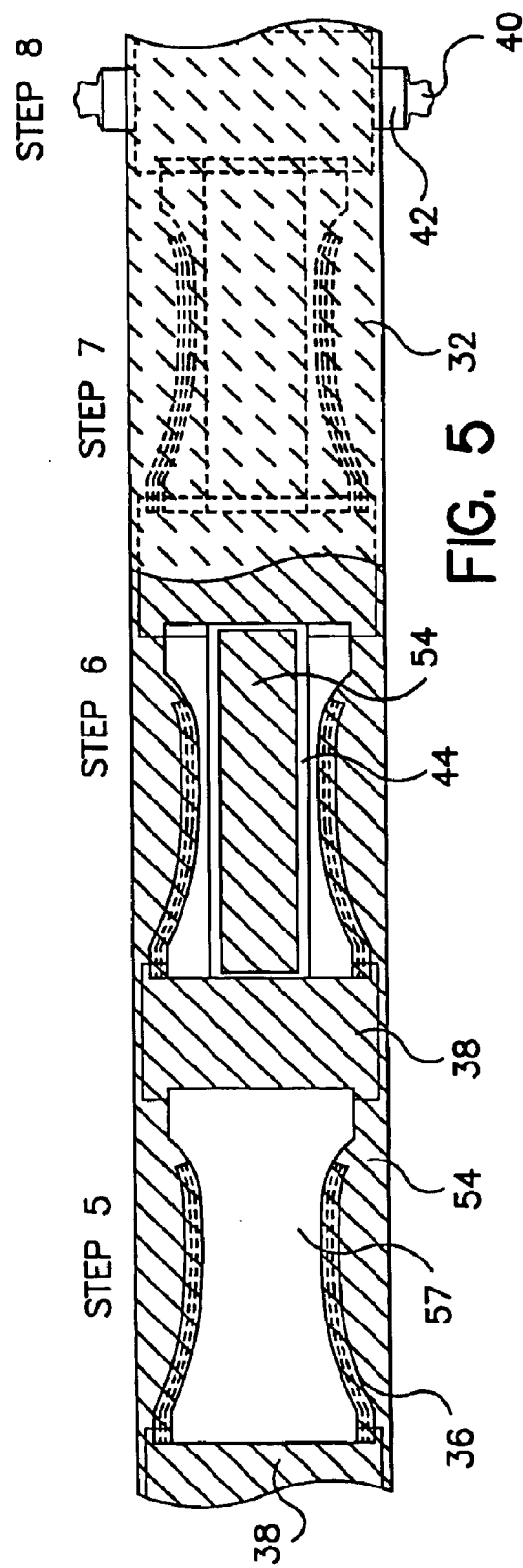

METHOD FOR MAKING A DISPOSABLE GARMENT HAVING SOFTER WAIST AND LEG CUFFS

BACKGROUND OF THE INVENTION

It is desirable that personal care absorbent articles, and especially garments such as diapers, training pants, or incontinence garments, without limitation referred to generically now for ease of explanation as "diapers", provide a close, comfortable fit about the waist and legs of the wearer and contain body exudates while maintaining skin health. In certain circumstances, it is also desirable that such garments are capable of being pulled up or down over the hips of the wearer to allow the wearer or care giver to easily pull the article on and easily remove the article. Other garment openings such as sleeve or pant cuffs and necklines may benefit from similar elasticizing.

Various schemes for producing elastic waistbands on disposable diapers have been proposed. Diaper waistbands are generally made by stretching an elastomer, applying the stretched elastomer to the diaper components, typically non-elastic in the waistband area, and allowing the elastomer to retract, thus gathering the attached diaper web components in the waistband area. The gathered waistband will then ungather when applied to a wearer, to give the waistband circumference some extension while the elastomer produces a retractive force holding the waistband snug to the wearer.

In another known method of making elastic waist bands, U.S. Pat. No. 4,968,313 issued Nov. 6, 1990 to Sabee, teaches the application of a relaxed elastic element to a relaxed diaper web component which is subsequently drawn or stretched to change the molecular orientation of the fibers of the web and permanently deform the fiber structure to produce a waist band of the gathered web and the retracted elastomer for the garment.

However, the gathered-material waistband arrangements of the known art may apply excessive force to the skin of the wearer resulting in discomfort, red marks on the skin and other undesirable effects. There further remains a need for alternative methods of making waistbands for disposable garments which provide a softer, more conformable fit to the wearer at the waist and leg openings, while continuing to provide ease and economy of manufacture, and adequate performance.

SUMMARY OF THE INVENTION

In response to the above discussion, an alternative method of elasticized garment opening construction is provided by the present invention which provides a softer, more conformable fit to the wearer at the waist and leg openings, while maintaining ease and economy of manufacture, and adequate performance against leakage. The method according to one embodiment of the present invention provides for reducing the number of material layers in the leg and waist elastic regions and utilizing barrier materials that are more flexible. Another aspect of the invention provides a portion of the liquid barrier function of the garment with waist and leg elastic materials which are liquid impermeable but vapor permeable. In another aspect, the invention provides a liquid retention portion of a garment with its own liquid barrier function to enable a softer more conformable outer layer to be used on the garment.

The person having ordinary skill in the art of disposable diaper manufacture will appreciate that the disposable diaper is generally made up of the layers of a substantially liquid-impermeable backsheet, a liquid-permeable topsheet and an liquid retention structure located between the backsheet and the topsheet. In order to be extendible any two joined layers must have compatible stretch to the limits of the desired processing parameters. In other words, the combined layers or webs, in those areas where the webs are fastened together, will be limited in the amount they may be stretched by the properties of the layer having the least amount of stretch.

The present invention presents an alternative way of making waistband and leg cuff elements, sometimes referred to collectively herein as "cuffs" by attaching soft, lightweight, and conformable material elastomers to the waistband and leg hole areas of the precursor garment, or more accurately, selected component webs of the precursor garment such as the backsheet. The elastomers may act as a liquid barrier. The waistband area backsheet and topsheet components of the present invention may be inherently extendible in the lateral, or longitudinal, or both, dimensions of the garment. The areas of the web having leg and waist elastics may be extendible in either of the elastic sense, i.e., with recovery; or the extensible sense, with little or no recovery. The elastomer may be applied in a stretched, or tensioned, condition to the elasticized areas of the extendible precursor garment web to achieve gathered waistbands and leg openings, either of which may sometimes be referred to hereinafter as "cuffs". When the diaper is placed on the wearer, the cuffs will be physically caused to laterally expand, thus forming a desirable snug fitting cuff area having extendible dimension and elastic tension.

Generally, the present invention provides a disposable absorbent article that defines a front waist section, a rear waist section, an intermediate section which extends between and connects the waist sections, a pair of laterally opposed side edges generally forming the leg cuffs, a pair of longitudinally opposed waist edges, a longitudinal direction and a lateral direction. Elastic waistbands and leg cuffs are provided in a unique fashion with selected light weight, conformable, and soft materials providing elasticity. Lightweight and soft backsheet and topsheet materials are provided as the only materials carrying the elasticized waist and leg cuffs to conform to the body of the wearer.

The absorbent article may also include other known components of diapers such as a pair of fasteners located on the laterally opposed side edges in one of the waist sections. In certain aspects, the disposable absorbent article may be provided in a prefastened, pant-like configuration such that the article can be pulled on or off over the hips of the wearer similar to conventional training pants. For example, the fasteners may refastenably attach the laterally opposed side edges in the front waist section to the laterally opposed side edges in the rear waist section to provide the pant-like, prefastened absorbent article prior to packaging the articles.

There are various ways to accomplish the present invention. For example, the diaper outer cover, or backsheet, and bodyside liner, or topsheet, or both, may be constructed to be extendible in the lateral dimension, shown generally herein as the cross machine direction (CD), and assembled into the precursor diaper. An untensioned elastomeric may be placed in the cuff regions of the topsheet or backsheet before joining in the diaper making process, i.e., converting the components into a garment in the case where an ungathered waistband is desired.

Alternatively, if a narrowed and gathered waistband area is desired, the elastomer will be applied with tension and the elastomeric will gather the waistband area. A doubly expandable waist band may be provided, with a first stage expansion taking out the gathers, and a second stage expansion expanding the material of the garment body.

A first exemplary embodiment of the present invention may include the precursor web having an extendible topsheet and an extendible backsheet with an untensioned elastomeric placed between them in at least one cuff area of the precursor garment. The extendible top sheet and backsheet may be elastic or extensible, or a combination thereof, to achieve selectable conformity of the garment to the wearer.

Generally, a backsheet according to the present invention may be a single, light nonwoven web which is left in a naturally hydrophobic condition but is otherwise unreinforced for barrier properties, unlike the prior art in which the backsheet is generally made to be a composite layer ensuring a high degree of liquid barrier properties. In place of the composite backsheet layer of the known art, a garment construction according to the present invention desirably utilizes a barrier layer for the absorbent section to provide a retention-barrier section behind only the absorbent area of the garment. Elastic waist and leg areas surrounding the absorbent area of the garment then provide a further liquid barrier as placed on the light nonwoven web of the backsheet, in addition to providing tensioned cuff, or opening, areas of the garment. A topsheet according to the present invention may be a single, light nonwoven web which is surfactant-treated to become hydrophilic. The topsheet may then be placed over the backsheet, to which the retention-barrier section and cuff elastomers have been applied, to complete a light, conformable, comfortably tensioned garment for the wearer. The retention-barrier section may be extendible or elastic.

BRIEF DESCRIPTION OF THE DRAWINGS

The present invention will be more fully understood and further advantages will become apparent when reference is made to the following detailed description of the invention and the drawings, in which:

FIG. 2 illustrates a process for forming a precursor absorbent section suitable for use with an embodiment of the present invention.

FIG. 3 illustrates a beginning manufacturing sequence of disposable diapers according to the present invention whereby the absorbent section of FIG. 2 is attached to a barrier material backing.

FIG. 4 illustrates a beginning manufacturing sequence of the conversion of various webs into disposable diapers according to the present invention with the longitudinal direction of the diapers being in the machine direction.

FIG. 5 illustrates an middle manufacturing sequence continuing on from the sequence of FIG. 4.

DEFINITIONS

Figure 1:
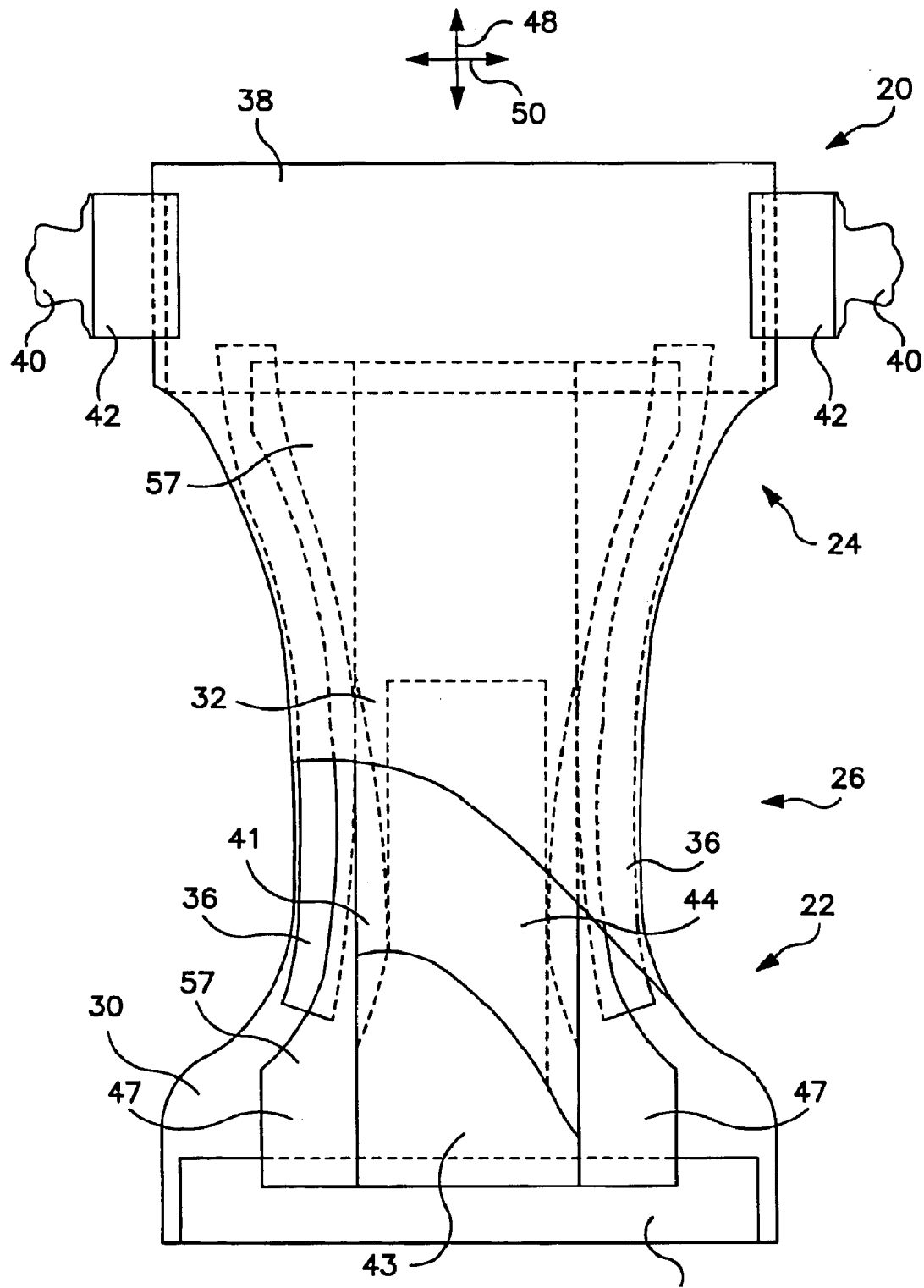
FIG. 1 representatively shows a partially cut-away, top plan view of the inward surface of an example of an article of the invention.

As used herein, the term "nonwoven web" or "nonwoven material" means a web having a structure of individual fibers, filaments or threads which are interlaid, but not in a regular or identifiable manner such as those in a knitted fabric or films that have been fibrillated. Nonwoven webs or materials have been formed from many processes such as, for example, meltblowing processes, spunbonding processes, and bonded carded web processes. The basis weight of nonwoven webs or materials is usually expressed in ounces of material per square yard (osy) or grams per square meter (gsm), and the fiber diameters usable are usually expressed in microns. (Note that to convert from osy to gsm, multiply osy by 33.91.)The term "fabrics" is used to refer to all of the woven, knitted and nonwoven fibrous webs.

As used herein, the terms "elastic", "elastomeric", and forms thereof, mean any material which, upon application of a biasing force, is stretchable, that is, elongatable, and which will substantially recover its elongation upon release of the stretching, elongating force. The term will include precursor elastomerics which are heat activated or otherwise subsequently treated after application to the precursor diaper structure to induce elasticity. The term "extendible" refers to a material which is stretchable in at least one direction but which may or may not have sufficient recovery to be considered elastic. The term "extensible" refers to a material which is stretchable in at least one direction but which does not have sufficient recovery to be considered elastic.

As used herein, the term "machine direction", or MD, means the length of a fabric in the direction in which it is produced. The term "cross machine direction", or CD, means the width of fabric, i.e., a direction generally perpendicular to the MD.

Words of degree, such as "about", "substantially", and the like are used herein in the sense of "at, or nearly at when given the manufacturing and material tolerances inherent in the stated circumstances" and are used to prevent the unscrupulous infringer from unfairly taking advantage of the invention disclosure where exact figures or absolutes are stated as an aid to understanding the invention.

"Precursor" as used herein means those components, materials, assemblies, or the like which are used or exist in the making of a finished diaper before its completion as a commercially ready product.

DETAILED DESCRIPTION OF THE PRESENTLY PREFERRED EMBODIMENTS

The various aspects and embodiments of the invention will be described in the context of disposable absorbent articles, and more particularly referred to, without limitation and by way of illustration only, as a disposable diaper. It is, however, readily apparent that the present invention could also be employed with other absorbent articles, such as feminine care articles, various incontinence garments, medical garments, and any other disposable garments, whether absorbent or not, needing an easily conformable cuff structure for elastic waistbands or leg opening areas. Typically, the disposable articles or garments are intended for limited use and are not intended to be laundered or otherwise cleaned for reuse. A disposable diaper, for example, is discarded after it has become soiled by the wearer.

FIG. 1 is a representative plan view of an absorbent article, such as disposable diaper 20, of the present invention in its flat-out, or unfolded state. Portions of the structure are partially cut away to more clearly show the interior construction of diaper 20. The surface of the diaper 20 which contacts the wearer is facing the viewer.

With reference to FIG. 1, the disposable diaper 20 generally defines a front waist section 22, a rear waist section 24, and an intermediate section 26 which interconnects the front and rear waist sections. The front and rear waist sections 22 and 24 include the general portions of the article which are constructed to extend substantially over the wearer's front and rear abdominal regions, respectively, during use. The intermediate section 26 of the article includes the general portion of the article that is constructed to cover the wearer's crotch region and extend between the legs. Thus, the intermediate section 26 is an area where repeated liquid surges typically occur in the diaper or other disposable absorbent article.

The diaper 20 includes, without limitation, an outer cover, or backsheet 30, a liquid permeable bodyside liner, or topsheet, 32 positioned in facing relation with the backsheet 30, and an absorbent body, or liquid retention structure 57, as further explained below, which is located between the backsheet 30 and the topsheet 32. The backsheet 30 has a length, or longitudinal direction 48, and a width, or lateral direction 50 which, in the illustrated embodiment, coincide with the length and width of the diaper 20. The liquid retention-barrier structure 57 generally has a length and width that are less than the length and width of the backsheet 30, respectively. Thus, marginal portions of the diaper 20, such as marginal sections of the backsheet 30, may extend past the terminal edges of the liquid retention-barrier structure 57. In the illustrated embodiments, for example, the backsheet 30 extends outwardly beyond the terminal marginal edges of the liquid retention-barrier structure 57 to form side margins and end margins of the diaper 20. The topsheet 32 is generally coextensive with the backsheet 30 but may optionally cover an area which is larger or smaller than the area of the backsheet 30, as desired.

To provide improved fit and to help reduce leakage of body exudates from the diaper 20, the diaper side margins and end margins may be elasticized with suitable elastic members, as further explained below. For example, as representatively illustrated in FIG. 1, the diaper 20 may include leg elastics 36 which are constructed to operably tension the side margins of the diaper 20 to provide elasticized leg bands, also referred to as leg cuff or leg areas, which can closely fit around the legs of the wearer to reduce leakage and provide improved comfort and appearance. Waist elastics 38 are employed to elasticize the end margins of the diaper 20 to provide elasticized waistbands. The waist elastics are configured to provide a resilient, comfortably close fit around the waist of the wearer.

Materials suitable for use as the leg elastics 36 and waist elastics 38 are particularly employed by the present invention to provide improved fit. Exemplary of such materials are liquid impermeable, vapor permeable, spunbond laminates (SBL), necked bonded laminates (NBL), and laminates of LYCRA (trademark) elastomeric and spunbond-meltblown-spunbond (SMS) nonwovens. Variants of elastomeric materials suitable for use with the present invention may occur to the person having ordinary skill in the art upon gaining an understanding of the invention as presented herein.

As is known, fastening means, such as hook and loop fasteners, with a hook portion shown at ref. no. 40, may be employed to secure the diaper on a wearer. Alternatively, other fastening means, such as buttons, pins, snaps, adhesive tape fasteners, cohesives, fabric-and-loop fasteners, or the like, may be employed. In the illustrated embodiment, the diaper 20 includes a pair of side panels 42 to which the fasteners 40 are attached. Generally, the side panels 42 are attached to the side edges of the diaper 20 in one of the waist sections and extend laterally outward therefrom. The side panels 42 may be elasticized or otherwise rendered elastomeric. For example, the side panels 42 may be an elastomeric material such as a neck-bonded laminate (NBL) or spunbond laminate (SBL) material. Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al. Examples of absorbent articles that include elasticized side panels and selectively configured fastener tabs are described in U.S. Pat. No. 5,496,298 issued Mar. 5, 1996 to Kuepper et al.; U.S. Pat. No. 5,540,796 to Fries; and U.S. Pat. No. 5,595,618 to Fries.

The diaper 20 may also include a surge management layer 44 (FIG. 5), located between the topsheet 32 and the liquid retention-barrier structure 57, to rapidly except fluid exudates and distribute the fluid exudates to the liquid retention-barrier structure 57 within the diaper 20. Examples of suitable surge management layers 44 are described in U.S. Pat. No. 5,486,166 to Bishop and U.S. Pat. No. 5,490,846 to Ellis.

The disposable diaper 20 may also include a pair of containment flaps 46 (FIG. 6) which are configured to provide a barrier to the lateral flow of body exudates. Such containment flaps 46 are generally well known to those skilled in the art. For example, suitable constructions and arrangements for containment flaps 46 are described in U.S. Pat. No. 4,704,96 issued Nov. 3, 1987, to K. Enloe.

The diaper 20 may be of various suitable shapes. For example, the diaper may have an overall rectangular shape, T-shape or an approximately hour-glass shape. In the shown embodiment, the diaper 20 has a generally I-shape. The diaper 20 further has a longitudinal direction 48, and a lateral direction 50. Other suitable components which may be incorporated on absorbent articles of the present invention may include waist flaps and the like which are generally known to those skilled in the art. Examples of diaper configurations suitable for use in connection with the instant invention which may include other components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996 to Hanson et al.

The various components of the diaper 20 are integrally assembled together employing various types of suitable attachment means, such as adhesive, ultrasonic bonds, thermal bonds or combinations thereof. In the shown embodiment, for example, the topsheet 32 and backsheet 30 may be assembled to each other and to the liquid retention-barrier structure 57 with lines of adhesive, such as a hot melt, pressure-sensitive adhesive. Similarly, other diaper components, such as the elastic members 36 and 38, fastening members 40, and surge layer 44 may be assembled into the article by employing the above-identified attachment mechanisms.

The illustrated diaper 20 includes distinctive waistband and leg cuff structures formed by applying an elastomeric 36, 38, respectively, to at least the backsheet 30 which is selected for its superior feel, light weight, vapor permeability, and desirably, an inherent hook attachment acceptance. One such material is a 0.6 osy spunbond nonwoven comprising polypropylene polymer filaments. The polypropylene spunbond nonwoven web is hydrophobic in its natural state and is therefore left untreated to provide such additional liquid barrier properties as are inherent in the web without additional reinforcement layers of films or the like typically used to provide liquid barrier properties. Thus, the backsheet will be lighter and more conformable than those backsheet materials typically used in the known art. The material is desirably extensible or elastic, dependent upon the particular application to which the personal care article is to be put. As known in the art, the backsheet 30 generally includes a fabric or material layer which may be operatively attached or otherwise joined to the other diaper layers to extend over a major portion of the outward surface of the article. It will occur to the person having ordinary skill in the art that if the backsheet is not used in conjunction with the diaper waistband, other layers used in the construction of a diaper may be similarly utilized according to the precepts of the present invention. Generally, it is desirable for simplicity of construction that the backsheet 30 remains the structural unit of choice for applying the waistband and leg opening elastomerics in the making of diapers according to the present invention.

Desirably, the backsheet 30 is constructed to be permeable to at least water vapor. For example, in particular embodiments, the backsheet 30 defines a water vapor transmission rate (WVTR) according to the Mocon Water Vapor Transmission Rate Test of at least about 100 g/sq.m/24 hr., desirably at least about 1200 g/sq.m/24 hr, more desirably at least about 2000 g/sq.m/24 hr., and even more desirably at least about 3000 g/sq.m/24 hr. in the non-extended condition. In such embodiments, the backsheet 30 may define a WVTR of from about 100 to about 30,000 g/sq.m/24 hr. Materials which have a WVTR less than those above may not allow a sufficient amount of water vapor diffusion out of the diaper and undesirably result in increased levels of skin hydration. A Mocon WVTR test is described in U.S. Pat. No. 6,156,421 issued Dec. 5, 2000 to Stopper et al.

The backsheet 30 can be composed of various materials that provide the desired property of substantial liquid impermeability. An outer surface of the garment may then be produced with the spunbond facing serving as a fastening material for fabric loop type fasteners. The backsheet may be elastic or extendible.

The topsheet 32, as representatively illustrated in FIG. 1, typically presents a body-facing surface that is compliant, soft-feeling, and non-irritating to the wearer's skin. Further, the topsheet 32 can be sufficiently porous to be liquid permeable, permitting liquid to readily penetrate through its thickness to reach the absorbent composite. The topsheet layer 32 is typically employed to help isolate the wearer's skin from liquids held in the liquid retention-barrier structure 57.

Various woven and nonwoven fabrics can be used for topsheet 32. For example, the topsheet may be composed of a meltblown or spunbond web of the desired fibers, and may also be a bonded-carded-web. Layers of different materials that may have different fiber deniers can also be used. The various fabrics can be composed of natural fibers, synthetic fibers or combinations thereof. The topsheet 32 may be composed of a substantially hydrophobic material, and the hydrophobic material may optionally be treated with a surfactant or otherwise processed to impart a desired level of wettability and hydrophilicity. In a particular embodiment of the invention, topsheet 32 can be a nonwoven, spunbond polypropylene fabric composed of about 1.0–5.0 denier fibers formed into a web having a basis weight of about 0.5 osy. The polypropylene spunbond nonwoven web is hydrophobic in its natural state and is therefore surfactant-treated to provide such additional liquid transmission properties as are needed for the web. Surfactants utilized with polypropylene spunbond nonwoven webs are known to those of skill in the art.

Desirably, the topsheet 32 is made from extendible materials for compatibility with the backsheet 30 as well as for reduced cost and improved manufacturing efficiency. Suitable extendible materials for use with the present invention may include nonwoven webs, woven materials and knitted materials which are inherently, or can be made, extendible or elastic. Such webs should be light weight and readily conformable according to the dictates of the present invention. Nonwoven fabrics or webs have been formed from many processes, for example, bonded carded web processes, meltblown processes and spunbond processes. The extendible material can be formed from at least one member selected from fibers and filaments of inelastic polymers. Such polymers include polyesters, for example, polyethylene terephthalate, polyolefins, for example, polyethylene and polypropylene, polyamides, for example, nylon 6 and nylon 66. These fibers or filaments are used alone or in a mixture of two or more thereof Suitable fibers may also include natural and synthetic fibers as well as bicomponent, multi-component, and shaped polymer fibers. Many polyolefins are available for fiber production according to the present invention, for example, fiber forming polypropylenes include Exxon Chemical Company's Escorene7 PD 3445 polypropylene and Himont Chemical Company's PF-304. Polyethylenes such as Dow Chemical's ASPUN7 6811A linear low density polyethylene, 2553 LLDPE and 25355 and 12350 high density polyethylene are also suitable polymers. The nonwoven web layer may be bonded to impart a discrete bond pattern with a prescribed bond surface area.

Desirably, both the backsheet 30 and the topsheet 32 are extendible in the lateral direction as set forth above for improved fit and performance of the waistband and the overall garment. The topsheet 32 and backsheet 30 may be connected or otherwise associated together in an operable manner. As used herein, the term "associated" encompasses configurations in which topsheet 32 is directly joined to the backsheet 30 by affixing the topsheet 32 directly to the backsheet 30, which is desirable according to the dictates of the present invention to keep overall weight and thickness in the cuff areas low, but may also include configurations wherein the topsheet 32 is indirectly joined to the backsheet 30 by affixing the topsheet 32 to intermediate members which in turn are affixed to the backsheet 30. The topsheet 32 and the backsheet 30 can, for example, be joined to each other in at least a portion of the diaper periphery by attachment mechanisms (not shown) such as adhesive bonds, sonic bonds, thermal bonds, pinning, stitching or any other attachment techniques known in the art, as well as combinations thereof.

For example, a uniform continuous layer of adhesive, a patterned layer of adhesive, a sprayed pattern of adhesive or an array of separate lines, swirls or spots of construction bonds may be used to affix the topsheet 32 to the backsheet 30. It should be readily appreciated that the above-described attachment mechanisms may also be employed to suitably interconnect, assemble and/or affix together the various other component parts of the garments or articles that are described herein.

The liquid retention-barrier structure 57 provides an absorbent structure for holding and storing absorbed liquids and other waste materials, such as the shown absorbent pad composed of selected hydrophilic fibers and high-absorbency particles. The liquid retention-barrier structure 57 may also be extendible or not extendible, although it should not interfere with the expanding of the cuff areas. The liquid retention-barrier structure 57 is positioned and sandwiched between the topsheet 32 and backsheet 30 to form the diaper 20. The liquid retention-barrier structure 57 has a construction that is generally compressible, conformable, non-irritating to the wearer's skin, and capable of absorbing and retaining body exudates. It will be understood that, for purposes of this invention, the liquid retention-barrier structure 57 is constructed to impart a barrier layer ability to aid in, or substantially take the place of, the outside layer liquid barrier abilities of the diaper in order to provide for a lighter backsheet in the overall construction of the garment.

Various types of wettable, hydrophilic fibrous material can be used to form the absorbent component parts of liquid retention-barrier structure 57. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed. The liquid retention-barrier structure 57 can include a matrix of hydrophilic fibers, such as a web of cellulosic fluff, mixed with particles of high-absorbency material. In particular arrangements, the liquid retention-barrier structure 57 may include a mixture of superabsorbent hydrogel-forming particles or fibers and synthetic polymer meltblown fibers, or a mixture of superabsorbent particles or fibers with a fibrous coform material including a blend of natural fibers and/or synthetic polymer fibers.

The hydrophilic fibers and high-absorbency particles may be configured to form an average composite basis weight which is within the range of about 400–900 gsm, although the range may be broader dependent upon the absorbents used. In certain aspects of the invention, the average composite basis weight is within the range of about 500–800 gsm, and alternatively is within the range of about 550–750 gsm to provide desired performance.

A substantially hydrophilic tissue wrapsheet 41 is employed in the exemplary embodiment to help maintain the integrity of the fibrous structure of the liquid retention-barrier structure 57. The tissue wrapsheet 41 is typically placed about the liquid retention-barrier structure over at least the two major facing surfaces thereof and composed of an absorbent cellulosic material, such as creped wadding or a high wet-strength tissue that may or may not be pleated. In one aspect of the invention, the tissue wrapsheet can be configured to provide a wicking layer which helps to rapidly distribute liquid over the mass of absorbent fibers including the liquid retention-barrier structure 57. The wrapsheet material on one side of the absorbent fibrous mass 43 may be bonded to the wrapsheet 41 located on the opposite side of the fibrous mass to effectively entrap the fibrous mass.

With reference to FIG. 1, each of the leg elastic members 36 may be a light weight nonwoven carrier layer with elastomeric strands, such as LYCRA (trademark) elastomeric, operatively attached to the carrier layer. Various mechanisms, such as adhesive, thermal bonds, sonic bonds, or the like as well as combinations thereof, can be employed to provide the desired attachments between the elastomeric strands and the carrier layer. For example, each leg elastic member may be composed of a laminate of the elastomeric strands sandwiched and held between a pair of carrier layers. The carrier layers may desirably be composed of a non-woven spun-meltblown-spunbond (SMS) fabric having a basis weight within the range of about 0.6 osy, but may optionally be composed of a polymer film material. For example, the carrier layers may be composed of a polypropylene spunbond nonwoven fabric, and the pair of carrier layers may be adhesively bonded together with a suitable pattern of adhesive, such as a swirl-pattern of pressure-sensitive adhesive. Alternatively, the leg elastic members may be made from an elastomeric barrier adhesive (EBA) such as available from Bostik-Findley Adhesives, Inc., Wauwatosa, Wis. under the trade designations Findley H2503 and H2504 or others cited herein, and may have nonwoven facings applied thereto.

The waist elastic elements 38 may desirably include a spunbond laminate of light weight nonwoven outer carrier layers with an elastomeric liquid barrier film, such as a KRATON (trademark) meltblown elastomer layer, available from Krayton Polymers USLLC of Belpre, Ohio; operatively attached between the carrier layers. Various mechanisms, such as adhesive, thermal bonds, sonic bonds, or the like as well as combinations thereof, can be employed to provide the desired attachments between the elastomeric layer and the carrier layers. The carrier layers may desirably be composed of a nonwoven polypropylene-spunbond fabric having a basis weight within the range of about 0.3 osy to about 0.7 osy, but may optionally be composed of a polymer film material.

The leg and waist elastic members 36, 38, respectively, may be affixed to the backsheet 30 or topsheet 32, or both, of the diaper 20 in any of several ways that are known in the art. For example, the elastic members may be ultrasonically bonded, heat and pressure sealed using a variety of bonding patterns, or adhesively bonded to the diaper with sprayed or swirled patterns of adhesive.

PROCESSING EXAMPLE

The following example is presented to provide a more detailed understanding of the invention. The example is representative, and is not intended to limit the scope of the invention.

With reference to FIGS. 2–6, means and method for constructing one embodiment of present invention, exemplified as a disposable diaper, are set forth.

Referencing FIGS. 2 and 3, retention-barrier portion 57 for the proposed invention may be constructed as discussed in the steps below.

Step 1: A web of barrier tissue 41 such as American Tissue 12.5 pound per ream white tissue from American Tissue, Inc. of Neenah, Wis. is fed into a first processing line.

Step 2: A fluff pad 43 which is approximately a 60:40 blend of superabsorbent material such as Favor SXM-880 superabsorbent from Stockhausen of Greensboro, N.C., and fiberized fluff pulp (16% hardwood) from Alliance Forest Products of Coosa Pines, Ala., is formed and deposited onto the barrier tissue 41 in a basically rectangular shape. The fluff pad 43 may be shaped so as to be more narrow when placed in a crotch region of the diaper, also as shown in FIG. 1.

Step 3: Barrier Tissue 41 is wrapped around the fluff pad 43 forming a continuous web of absorbents 45.

Step 4: A web of substantially liquid impermeable water vapor permeable barrier material 47 such as SMS, fluorocarbon treated SMS, microporous film, inherently breathable film, etc., is fed into the process. In some alternate embodiments of this invention it may be desirable that this web be extensible or elastic.

Step 5: A web of spacer layer 49 such as 0.8 osy SMS can be laminated to the barrier web 47. The spacer layer 49 may act as a ventilation layer to insulate the backsheet 30 from the liquid retention-barrier structure 57 to reduce the dampness of the garment at the exterior surface of the backsheet 30.

Step 6: The continuous web of absorbents 45 from Step 3 is laminated to the spacer layer web 54, if present, or directly to the barrier web 47, thereby forming a continuous web of retention-barrier material 51.

Step 7: Leg openings 53 are cut into the side margins 55 of the composite retention-barrier web 51.

Step 8: The continuous web of retention-barrier material 51 is then cut into individual retention-barrier portions 57.

Referencing FIGS. 4 and 5, the absorbent article construction of the proposed invention is completed on a converting line, i.e. converting materials to a finished product, as shown and discussed below.

Step 1: A nonwoven backsheet 30 such as 0.6 osy spunbond is fed into the process. In alternate embodiments of this invention this web may desirably be extensible or elastic.

Step 2: Waist elastic elements 38, desirably being a substantially liquid impermeable and water vapor permeable elastomeric material, such as an SBL laminate, may be elongated, i.e. tensioned, and then adhered to topsheet web 30.

Step 3: Leg elastic elements 36, desirably being a substantially liquid impermeable and water vapor permeable elastomeric material, such as a laminate of LYCRA (trademark) elastomeric from E. I. DuPont de Nemours and Co., of Wilmington, Del., and SMS nonwoven; or EBA and spunbond nonwoven, are elongated and then adhered to topsheet web 30.

Step 4: An adhesive 54 such as Disposamelt 34-5611 RMS 274 is applied to backsheet 30.

Step 5: The individual retention-barrier portions 57 are laminated to the backsheet 30 in a position between, and slightly overlapping leg elastic members 36 and waist elastic members 38.

Step 6: A liquid distribution, or surge management, layer 44, such as a through air bonded carded web (TABCW) surge composite, is adhesively laminated to the retention-barrier portion 57 with an adhesive 54 such as Disposamelt 34-5611. The adhesive 54 is desirably also applied in this application to the top surface of the surge management layer 44.

Step 7: A topsheet 32, indicated by broken-cross hatching, is desirably formed of a web such as a porous liquid permeable 0.5 osy spunbond nonwoven material, is then laminated, adhered, or otherwise attached over and to the previous web components on the converting line. In some alternate embodiments of this invention it may desirable that the topsheet 32 be extensible or elastic to the same degree as the backsheet 30 and the barrier sheet 47.

Step 8: A system of separately provided side panels that form fastening members 40 for the article, composed e.g., of a fastening material such as VELCRO 851 hook, from Velcro U.S.A., Inc. of Manchester, N.H., on a carrier sheet of 1.25 osy SMS, and an elastic side panel member 42 such as Necked Bonded laminate, may be adhesively and/or ultrasonically laminated to the precursor garment.

Figure 6:
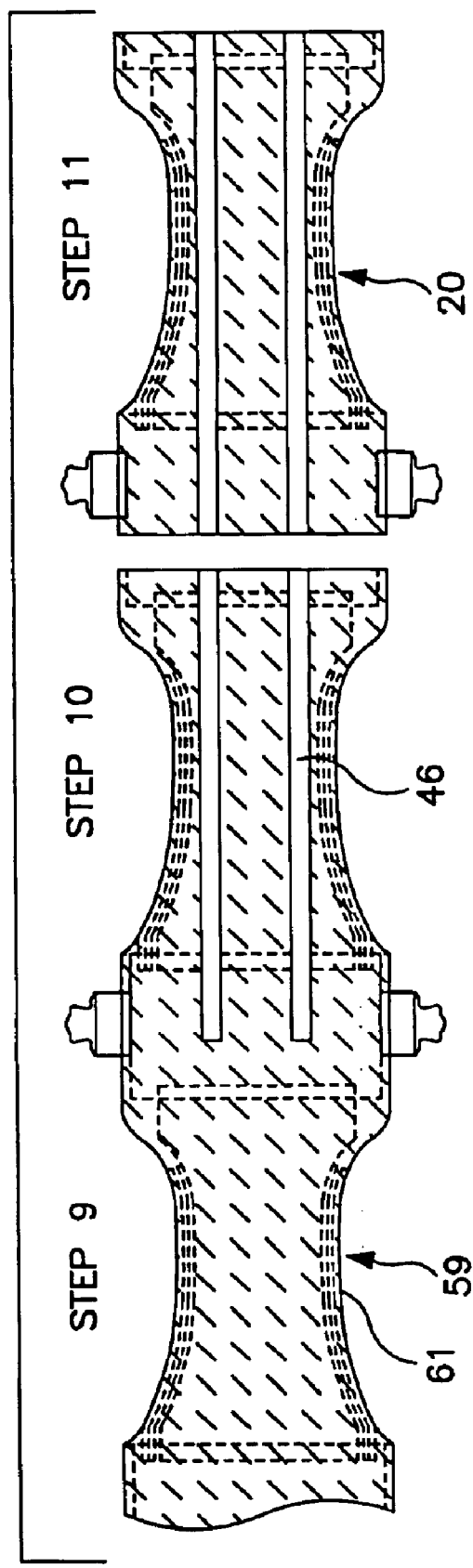
FIG. 6 illustrates an ending manufacturing sequence continuing on from the sequence of FIG. 5 and culminating in the individuation of product diapers from the precursor web.

Referencing FIG. 6, at Step 9: Leg openings 59 are cut into the diaper side margins 61.

Step 10: A system of containment flaps 46 may then be adhesively laminated to the web. The flaps may be composed of materials such as two elastic strands of GLOSPAN S7 spandex fiber 700 denier (777 decitex), from RadicSpandex Corp. of Fall River, Mass., laminated to a nonwoven web such as blue SMS 0.65 osy.

Step 11: The precursor web is then cut into individual disposable diapers 20. The diaper 20 can then be folded if desired (not shown).

It will thus be appreciated by those of skill in the art that the disposable diaper 20, as assembled using the proposed materials and methods of manufacture, has softer leg elastic elements 36 and waist elastic elements 38 because these elements have fewer layers and utilize more flexible materials than conventional diaper designs. The reduced stiffness of the elastomers requires less force to extend and contract providing improved conformance to the users body with less tension thereby providing enhanced comfort. Additionally, both the leg and waist elastic materials 36, 38 may provide liquid barrier functions, as may the retention-barrier section 57.

While the invention has been described in detail with respect to specific embodiments thereof, it will be appreciated that those skilled in the art, upon attaining an understanding of the foregoing may readily conceive of alterations to, variations of, and equivalents to these embodiments. Accordingly, the scope of the present invention should be assessed as that of the appended claims and any equivalents thereto.

We claim:

1. A method of making an absorbent personal care product comprising:
   a) supplying a retention-barrier composite web having an absorbent material adhered to a liquid barrier sheet and cut to individual product lengths;
   b) providing a soft and flexible backsheet;
   c) adding soft and flexible waist elastics to the backsheet;
   d) adding soft and flexible leg elastics to the backsheet;
   e) coating the construction of steps b)–d) with adhesive and adhering the retention-barrier composite web substantially between the waist and leg elastics to the backsheet;
   f) adhering a fluid distribution layer over and within the central portion of the retention-barrier composite web;
   g) adhering a soft and flexible topsheet over the construction of steps a)–f) to create a precursor product web; and
   h) cutting the precursor product web into individual absorbent personal care products.

2. The method of making an absorbent personal care product according to claim 1, wherein the liquid barrier sheet is liquid impermeable.

3. The method of making an absorbent personal care product according to claim 1, wherein the liquid barrier sheet is vapor permeable.

4. The method of making an absorbent personal care product according to claim 1, wherein the liquid barrier sheet is selected from one of the group including: SMS, fluorocarbon treated SMS, microporous film, and inherently breathable film.

5. The method of making an absorbent personal care product according to claim 1, wherein the liquid barrier sheet is elastic.

6. The method of making an absorbent personal care product according to claim 1, wherein the liquid barrier sheet is extensible.

7. The method of making an absorbent personal care product according to claim 1, wherein the backsheet is hydrophobic.

8. The method of making an absorbent personal care product according to claim 1, wherein the backsheet is vapor permeable.

9. The method of making an absorbent personal care product according to claim 1, wherein the backsheet is 0.6 osy spunbond.

10. The method of making an absorbent personal care product according to claim 1, wherein the backsheet is elastic.

11. The method of making an absorbent personal care product according to claim 1, wherein the backsheet is extensible.

12. The method of making an absorbent personal care product according to claim 1, wherein the waist elastic is liquid impermeable.

13. The method of making an absorbent personal care product according to claim 1, wherein the waist elastic is vapor permeable.

14. The method of making an absorbent personal care product according to claim 1, wherein the waist elastic is an SBL laminate.

15. The method of making an absorbent personal care product according to claim 1, wherein the leg elastic is liquid impermeable.

16. The method of making an absorbent personal care product according to claim 1, wherein the leg elastic is vapor permeable.

17. The method of making an absorbent personal care product according to claim 1, wherein the leg elastic is an elastic and SMS nonwoven laminate.

18. The method of making an absorbent personal care product according to claim 1, wherein the topsheet is liquid permeable.

19. The method of making an absorbent personal care product according to claim 1, wherein the topsheet is a porous 0.5 osy spunbond.

20. The method of making an absorbent personal care product according to claim 1, wherein the top sheet is elastic.

21. The method of making an absorbent personal care product according to claim 1, wherein the topsheet is extensible.

22. A method of making an absorbent personal care product comprising, the steps, in the order stated, of:
   a) creating a retention-barrier composite web on a first component line by:
      i) wrapping a fluff pad in tissue forming a continuous retention web;
      ii) feeding an extendible, vapor-permeable, liquid barrier sheet material into the first component line;
      iii) adhering a spacer layer on the barrier sheet;
      iv) laminating the retention web to the spacer layer thereby creating a retention-barrier composite web;
      v) cutting leg openings in the retention-barrier composite web; and
      vi) cutting the retention-barrier composite web to individual garment lengths;
   b) creating a precursor product web on a conversion line by:
      i) feeding a soft and flexible backsheet into the conversion line, the backsheet being elastic or extensible;
      ii) adding soft and flexible waist elastics to the backsheet;
      iii) adding soft and flexible leg elastics to the backsheet;
      iv) coating the construction of steps i)–iii) with adhesive and adhering the retention-barrier composite web thereto;
      v) adhering a fluid distribution layer over and within the central portion of the retention-barrier composite web;
      vi) adhering a soft and flexible topsheet over the whole construction of steps i)–v), the topsheet being elastic and extensible;
      vii) cutting leg holes in the backsheet and the topsheet and leaving said leg elastics adjacent the leg holes; and
      viii) cutting the precursor product web into individual absorbent personal care products.

23. An absorbent personal care product consisting of:
   a) a retention-barrier composite web having an absorbent material adhered to an extendible vapor-permeable, liquid barrier sheet and cut to individual product lengths;
   b) an extendible soft and flexible backsheet having soft and flexible waist elastics adhered to the backsheet and tensioned soft and flexible leg elastics adhered to the backsheet;
   c) the retention-barrier composite web adhered to the backsheet in an area between the waist elastics and the leg elastics;
   d) a fluid distribution layer adhered over and within the central portion of the retention-barrier composite web; and
   e) an extendible soft and flexible topsheet adhered to the soft and flexible backsheet and covering the retention-barrier composite web, the fluid distribution layer, the waist elastics and the leg elastics.

24. The absorbent personal care product of claim 23 further consisting of the retention-barrier composite laying entirely between the leg and waist elastics.

25. The absorbent personal care product of claim 24 further consisting of containment flaps.

* * * * *